(12) United States Patent
Kerr et al.

(10) Patent No.: US 10,328,186 B2
(45) Date of Patent: *Jun. 25, 2019

(54) METHOD AND APPARATUS FOR TREATMENT OF PLEURAL EFFUSION

(71) Applicant: PFM MEDICAL, INC., Carlsbad, CA (US)

(72) Inventors: Marshall Kerr, Carlsbad, CA (US); Michael Vaillancourt, Carlsbad, CA (US)

(73) Assignee: PFM MEDICAL, INC., Carlsbad, CA (US)

( * ) Notice: Subject to any disclaimer, the term of this patent is extended or adjusted under 35 U.S.C. 154(b) by 838 days.

This patent is subject to a terminal disclaimer.

(21) Appl. No.: 14/336,968

(22) Filed: Jul. 21, 2014

(65) Prior Publication Data

US 2014/0330228 A1  Nov. 6, 2014

Related U.S. Application Data

(63) Continuation of application No. 12/842,010, filed on Jul. 22, 2010, now Pat. No. 8,784,394.

(60) Provisional application No. 61/227,559, filed on Jul. 22, 2009.

(51) Int. Cl.
*A61M 1/00* (2006.01)
*A61M 39/24* (2006.01)
*A61M 39/10* (2006.01)

(52) U.S. Cl.
CPC ........ *A61M 1/0049* (2013.01); *A61M 1/0023* (2013.01); *A61M 39/24* (2013.01); *A61M 2039/1094* (2013.01); *A61M 2039/242* (2013.01); *A61M 2039/2406* (2013.01); *A61M 2202/0492* (2013.01); *A61M 2210/101* (2013.01)

(58) Field of Classification Search
CPC .... A61M 1/005; A61M 1/0078; A61M 1/008; A61M 1/0086; A61M 1/04; A61M 2039/1033; A61M 2039/1038; A61M 2039/1094; A61M 39/18

See application file for complete search history.

(56) References Cited

U.S. PATENT DOCUMENTS

| | | | | |
|---|---|---|---|---|
| 5,484,401 A | * | 1/1996 | Rodriguez | A61M 1/008 604/28 |
| 5,738,656 A | * | 4/1998 | Wagner | A61M 1/0084 604/119 |
| 6,059,484 A | * | 5/2000 | Greive | A61M 25/09041 128/912 |

(Continued)

*Primary Examiner* — Peter S Vasat
(74) *Attorney, Agent, or Firm* — Donn K. Harms

(57) ABSTRACT

A device for the drainage of a pleural effusion through an operatively engaged chest tube in the chest wall. The device employs a check valve situated between a vacuum source communicating with the chest tube to prevent reversal of the fluid flow out of the patient's body and possible contamination. A valve mounted on a vacuum bottle provides user control of communication of negative pressure from the vacuum bottle to the chest tube. Opening the valve on the bottle communicates negative pressure to the chest tube relative to the pressure in the tube thereby initiating a fluid flow out of the tube and the patient. Once the valve on the bottle is closed, fluid flow ceases and the check valve prevents reversal of the flow.

7 Claims, 2 Drawing Sheets

(56) References Cited

U.S. PATENT DOCUMENTS

| | | | |
|---|---|---|---|
| 2005/0197647 A1* | 9/2005 | Dolliver | A61M 1/008 604/541 |
| 2007/0129707 A1* | 6/2007 | Blott | A61F 13/00068 604/543 |
| 2010/0042021 A1* | 2/2010 | Hu | A61M 1/0009 601/6 |
| 2010/0274229 A1* | 10/2010 | Duocastella Codina | A61M 1/0011 604/543 |
| 2011/0028920 A1* | 2/2011 | Johannison | A61M 1/0088 604/319 |

* cited by examiner

METHOD AND APPARATUS FOR TREATMENT OF PLEURAL EFFUSION

This is a Continuing Application to U.S. patent application Ser. No. 12/842,010 filed on Jul. 22, 2010 which claims priority to U.S. Provisional Application No. 61/227,559 filed on Jul. 22, 2009, both of which are incorporated herein in their entirety by reference.

BACKGROUND OF THE INVENTION

1. Field of the Invention

The invention herein disclosed relates to medical devices for drainage of fluids from a patient during treatment. More particularly it relates to a system for drainage of fluid which unnaturally collects in the pleural space adjacent to the lung of a patient.

2. Prior Art

Pleural effusion is a medical condition which occurs when too much fluid collects in the pleural space of a patient. The pleural space is located in the chest cavity between the two layers of the pleura. It is more commonly known as "water on the lungs." Symptoms of such include: shortness of breath, chest pain, gastric discomfort, and coughing.

In humans, there are two thin membranes located in the chest cavity. One such membrane is the visceral pleura which is a lining of the lungs. A second such membrane is the parietal pleura which covers the inside of the chest wall.

In healthy individuals, there are small blood vessels in these pleural linings which produce a small amount of fluid continually. This fluid provides a lubricant for the opposing two pleural membranes allowing them to slip and glide smoothly against each other another during the individual's breathing movements.

Should extra fluid accumulate, that excess fluid is taken up by blood and lymph vessels, thereby maintaining a delicate balance of sufficient fluid for lubrication but not too much to cause problems. However, when an individual either produces too much fluid or some other internal problem prevents normal body removal, the result is an excess of pleural fluid which forms the pleural effusion. The most common causes of pleural effusion are diseases of the heart or lungs or an inflammation or infection of the pleura.

The accumulation of fluid, especially in patients who are already ill, is physically very uncomfortable. It can make it hard, if not painful, for the patient to breathe along with secondary infections which can exacerbate an ill patient's condition causing further deterioration. Consequently, conventional treatment calls for the removal of the excess fluid causing the pleural effusion for both the patient's comfort and their well being.

There are many devices and methods employed by medical professionals to drain excess fluid which accumulates in such pleural effusions. A widely used device and method employs a catheter or tube which is inserted through the chest wall such that the axial cavity of the tube is in communication with the pleural space where the fluid is accumulating. At a distal end of the tube, exterior to the patient's body, a vacuum source is engaged to the axial cavity to pull the fluid from the cavity. The distal end of the tube must be sealed when not being employed under negative air pressure or air and contaminated fluids will leak back into the chest cavity through the axial cavity.

One popular device for this treatment features a duckbill valve on the distal end of the tube leading from the patient's chest. A tube, under negative pressure, is inserted through the duckbill valve and evacuates fluid from the chest tube and chest. Once the tube is removed from the valve it reseals on its own.

However, using a duckbill, or other tube-insertion activated valve has recently been found to be a source of danger in treating the patient. Because the valve is activated by the exterior of a catheter or tube inserted between two internally housed biased blades, the blades are subject to contamination from bacteria and contaminants on the exterior of the inserted tube or from the interior of the tube once so inserted.

Removal of the inserted vacuum tube leaves the valve members inside their housing in a position where they cannot be cleaned. Bacteria, viruses, and other contaminants can thus be positioned within the housing of the duckbill valve safely protected from the air outside and in contact with an excellent food source in the form of leftover pleural fluid inside the valve. The bacteria, viruses or other contaminants also have a clear pathway to the interior of the chest cavity through the axial cavity of the chest tube. The design is thus inherently flawed in that it cannot be cleaned and is subject to constant contamination by tube insertion into the valve to activate it.

There are other systems for draining the pleural area inside the chest cavity but those with a chest tube which must have a sealing valve on the distal end are all subject to contamination.

As such, there exists an unmet need for a device and method which will employ a chest tube to drain fluid from a pleural effusion but is resistant by design to potential introduction of bacteria, viruses, and contaminants during use. Such a device should employ a connection at the distal end of the chest tube, which may be cleaned and then sealed when not in use to maintain it in a sterile condition. Such a device should allow for multiple drainage sessions, using vacuum sources which are easily engaged to the distal end of the chest tube, in a manner that does not introduce bacteria or viruses or such into the axial cavity leading to the patient's chest. Such a device should avoid the use of hard to clean tubular inserts, which most certainly over time will introduce contaminants or pathogens into the chest tube.

SUMMARY OF THE INVENTION

The disclosed device and method herein provide a novel remedy for the problems of conventional pleural drainage systems.

The device employs a chest tube having a first end adapted to contact and drain fluid from the pleural effusion into an axial cavity leading to a proximal end of the chest tube located outside the patient's body. Adjacent to the proximal end is a pressure activated check valve. This valve prevents a reverse flow and communication with the axial cavity of the chest tube, unless air pressure at the proximal end of the chest tube, in the axial cavity, is negative, relative to air pressure inside the body of the patient.

By employing negative air pressure to activate fluid flow through the axial cavity, and prevent backflow, air and fluid always moves in a direction away from the chest cavity, and out of the chest tube, whenever the check valve is opened by the applied negative pressure. This action by the check valve prevents both air and pathogens from entering the axial cavity where they can reach the chest, since the only time the axial cavity communicates with the exterior of the patient is on the occurrence of negative pressure pushing air and fluid out of the axial cavity of the chest tube and away from the patient. Cessation of negative pressure to the check valve at the proximal end of the chest tube, causes an immediate closure of the check valve thereby blocking pathogen entrance before it can happen.

Engagement of the negative pressure to the axial cavity at the proximal end of the chest tube is through the engagement of a male luer lock to a mating threaded luer docking component engaged to the proximal end of the chest tube. A central cavity of the docking component communicates with the axial cavity of the chest tube and with the fluid exiting the pleural effusion the check valve is opened by negative pressure in the central cavity. The negative pressure in the central cavity is provided by a vacuum source such as a bottle or a pump having a catheter with a conduit formed therein which is engaged to the male luer lock at a proximal end of the catheter. The luer lock has a passage therethrough communicating with the conduit of the catheter.

In use, once the luer lock is engaged upon the docking component, a seal is formed by the threaded engagement and an O-ring or pliable washer or other sealing means. This places the conduit, leading to the vacuum source, in a sealed communication with the axial passage of the chest tube. Thereafter, once the vacuum or negative pressure is placed in communication with the conduit of the catheter, it is communicated to the axial passage opening the check valve and initiating a flow of fluid away from the pleural cavity so long as there is negative pressure in sealed communication with the axial cavity.

To further protect the patient during long term use, the threadably engaged luer lock employs a U-shaped guide to align it with the central cavity of the docking component. This is most important in that it provides the convenience of a means of alignment of the luer lock with its docking component, while also providing an open slot to allow cleaning of the inside of the U-shaped guide to prevent any contaminants or pathogens from communicating with the central cavity. The central cavity of the docking component may be capped when not in use and is also easily cleaned.

The result is a device and method much safer for the patient through the provision of a one-way flow of fluid out of the pleural cavity and cessation of flow, once the negative pressure is removed, thereby preventing pathogen migration into the chest through the very chest tube being used to aid the patient.

With respect to the above description, before explaining at least one preferred embodiment of the disclosed pleural effusion drainage apparatus, it is to be understood that the invention is not limited in its application to the details of operation nor the arrangement of the components or steps in the method set forth in the following description or illustrations in the drawings. The various methods of implementation and operation of the disclosed pleural effusion drainage device are capable of other embodiments and of being practiced and carried out in various ways which will be obvious to those skilled in the art once they review this disclosure. Also, it is to be understood that the phraseology and terminology employed herein are for the purpose of description and should not be regarded as limiting.

Therefore, those skilled in the art will appreciate that the conception upon which this disclosure is based may readily be utilized as a basis for designing of methods and systems for carrying out the several purposes of the present invention which provides for drainage of a pleural effusion and elimination of chest cavity contamination and pathogen migration which can be caused by conventional such systems. Therefore, the objects and claims herein should be regarded as including such equivalent construction, steps, and methodology insofar as they do not depart from the spirit and scope of the present invention.

Further objectives of this invention will be brought out in the following part of the specification wherein detailed description is for the purpose of fully disclosing the invention without placing limitations thereon.

It is an object of this invention to provide a drainage device for pleural effusions which is easily employed by trained and untrained users.

It is another object of this invention to provide such a system which, by design, provides means to sterilize conduits and thereby prevents migration of pathogens outside the patient's body into the chest tube and chest where it can cause infection.

These together with other objects and advantages which become subsequently apparent reside in the details of the construction and operation of pleural effusion drainage system and method herein as more fully hereinafter described and claimed, reference being had to the accompanying drawings forming a part thereof, wherein like numerals refer to like parts throughout.

BRIEF DESCRIPTION OF DRAWING FIGURE

DETAILED DESCRIPTION OF THE PREFERRED EMBODIMENTS OF THE INVENTION

Figure 1A:
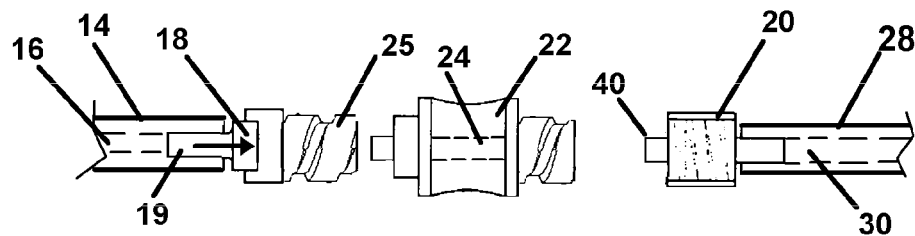
FIG. 1a is an enlargement of a preferred mode of components providing the sealed communication of negative pressure to the chest cavity through the chest tube.

Referring now to the FIGS. 1-4, the device 10 and method herein drains fluid from pleural effusions 12 and other points of ongoing fluid accumulation in the body of a patient.

In use, the device 10 is engaged with an operatively placed chest tube 14 having a first end configured for sealed communication with a catheter 28 having a communicated negative pressure therein, and thereby cause a draining of fluid from the pleural effusion 12. The chest tube 14 is configured to communicate operatively through the patient's chest wall 13. Fluid entering the distal end of the chest tube 14 is communicated into an axial cavity 16 in a sealed communication at the proximal end of the chest tube 14 with negative pressure emanating from a catheter 28 also in sealed communication with the axial cavity 16 by way of the check valve 18.

The pressure activated check valve 18 is in a sealed engagement in the pathway formed by the sealed communication between the axial conduit 30 of the catheter 28 and the axial cavity 16. The check valve 18 is so situated to selectively interrupt the communication between the axial cavity 16 of the chest tube 14 and the axial conduit 30 of the catheter 28 such as at a position on or adjacent to or upon the proximal end of the chest tube 14 which is positioned outside the body of the patient at the opposite end from the distal end which is the implanted portion of the chest tube 14. The check valve 18 which defaults to a closed position when not subjected to negative pressure communicated from the axial conduit 30, provides a seal for the axial cavity 16 and more importantly, a means to prevent reverse flow of fluid or contaminants from the proximal end of the chest tube 14 toward the distal end within the chest cavity thereby preventing contaminants from outside the body from gaining access thereto.

During employment of the device 10, with the check valve 18 engaged in a sealed engagement at or adjacent to the proximal end of the chest tube 14, and in the default closed position, all reverse flow through the axial cavity 16 from outside the body is prevented. The check valve 18 may be actuated to its open position by communication of negative pressure to the exit end of a central conduit 19 running through the check valve 18.

Switched to an open position the check valve 18 opens the central conduit 19 providing a sealed communication between the first end of the check valve 18 engaged to the axial cavity 16 at of the chest tube 14 and the second end of the check valve 18 opposite the first end engaged to the axial conduit 30 of the catheter 28. In this position the central conduit 19 at the first end of the check valve 18 communicates in a sealed engagement with the axial cavity 16 at the proximal end of the chest tube 14. Thus in the open position, the central conduit 19 communicates through the check valve 18, to a sealed communication with the axial cavity 16 forming a sealed communication between the vacuum source, and the intake of the axial cavity 16 at the distal end of the chest tube 14 implanted in the patient. The negative pressure so communicated initiates a one way flow, toward the check valve 18. In the default closed or non-open position, this communication through the central conduit 19 of the check valve 18 with the axial cavity 16 is blocked as is reverse fluid flow and entry into the axial cavity 16.

Actuation of the check valve 18 to the open position, in the current mode of the device 10, is achieved by the communication of negative pressure to the central conduit 19 at the second end of the check valve 18. This may be a direct communication from a negative pressure source, or through other components as pictured in the drawings. The resulting flow of fluid only flows through the axial cavity 16 in a direction away from the distal end in the chest cavity and out of the axial cavity 16 through the central conduit 19. This flow only occurs when negative pressure is communicated to the central conduit 19 through the second end of the check valve 18. Upon termination of the negative pressure communication to the second end of the check valve 18, it closes the central conduit 19 and prevents any flow through the proximal end of the chest tube 14 toward the distal end of the chest tube 14 implanted in the chest of the patient by an immediate closure of the check valve 18. Thus, as noted, no fluid or particulate or contaminants or air may enter the axial cavity 16 and flow the reverse direction since such is prevented during periods where netative pressure ceases causing return of the default closure of the check valve 18.

Communication of the negative pressure through the central conduit 19 and then to the axial cavity 16 at its communication with the central conduit 19, is currently provided using means for sealed engagement of the axial cavity 16 with the central conduit 19 and a second means for sealed engagement of a negative pressure source to the central conduit 19 at the second end of the check valve 18. As noted, the connection of negative pressure to the central conduit 19 may be direct, or may have other components in between. Currently such means for sealed engagement of the axial cavity 16 with the central conduit 19 is achieved using engagement of a male luer lock 20 to a mating threaded docking component 22 in operative sealed engagement with the proximal end of the chest tube 14. A passage 24 within the docking component 22, communicates between the axial cavity 16 of the chest tube 14 and the central conduit 19 of the check valve 18 forming a single sealed passage to communicate and drain fluid exiting the pleural effusion 12 through the axial cavity 16 and the central conduit 19 to then exit the first end of the check valve 18. The fluid flow in this fashion is allowed in one direction only.

It should be noted that while the connectors employed for the various sealed engagements of the chest tube 14 and the catheter 28 and the check valve 18 are shown as luer style connectors, those skilled in the art will realize upon reviewing this application, that many other connectors and connections may be employed to achieve the sealed engagements required to form the pathway between the distal end of the chest tube 14, through the check valve 18 and through the catheter 28 to an exit, so long as they accommodate the closure of the check valve 18 in a manner that prevents any backflow of fluid or contaminants into the chest tube 14. Currently luer lock style connectors are preferred as the medical industry has an installed base of such.

Further, those skilled in the art will realize that other means of inducing the check valve 18 to open by a communication of negative pressure to an actuator of the check valve 18 and such are anticipated within the scope of this application. However currently, experimentation has shown that communication of negative pressure to the central conduit 19, at the second end of the check valve 18, works well to provide a means to prevent backflow of fluid and contaminants into the chest tube 14 since communication into the axial cavity 16 of the chest tube 14, from the first end of the check valve 18, is prevented immediately upon closure of the check valve 18.

Currently, this communication of negative pressure to the central conduit 19 at the second end of the check valve 18, is provided by a vacuum source such as a vacuum bottle 26 or a pump communicating negative pressure through an axial conduit 30 of a catheter 28 where the axial conduit 30 is placed in a sealed engagement at one end to the central conduit 19 at the second end of the check valve 18.

Currently means to control this communication of negative pressure to activate the check valve 18 and initiate and control the one-way flow of fluid is achieved by employing an actuator on a second valve 36, which is opened between a vacuum source and its sealed communication with the axial conduit 30 to thereby communicate the negative pressure to the first end of the central conduit 19 of the check valve 18. Means for sealed engagement of the axial conduit 30 to the central conduit 19 is as noted, currently provided by engagement of the luer lock 20 which is in operative sealed engagement with the catheter 28 at a first end of the luer lock 20 opposite a threaded end of the luer lock 20.

Figure 1:
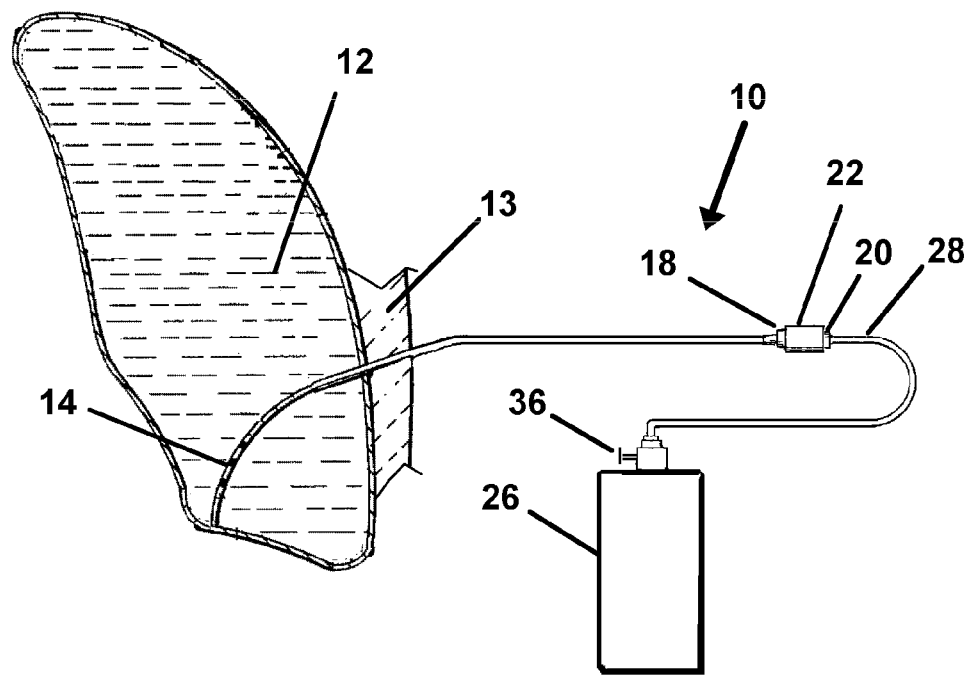
FIG. 1 is a graphic depiction of the device being employed through the chest wall to drain fluid from the chest cavity of a patient.
Figure 2:
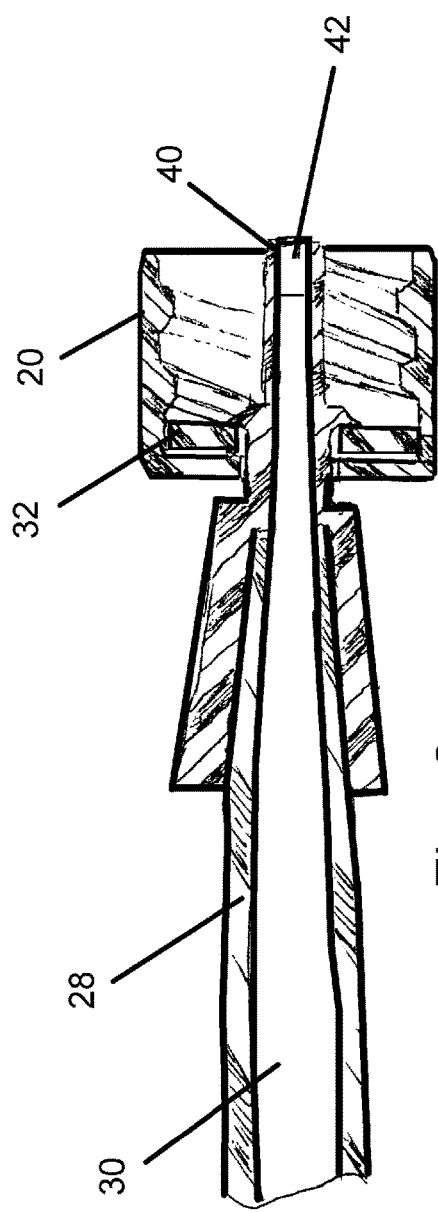
FIG. 2 depicts a cut away view through a connector adapted for sealed engagement with the docking component.
Figure 4:
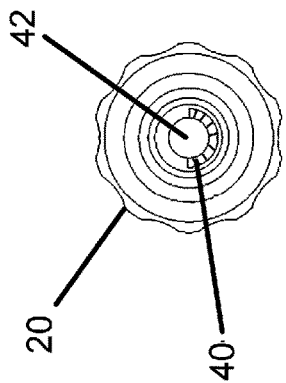
FIG. 4 depicts an end view of FIG. 3 showing an axial passage running through the sealing connector of FIG. 3 which is placed in sealed communication with a conduit connected to a vacuum or negative pressure source.
Figure 3:
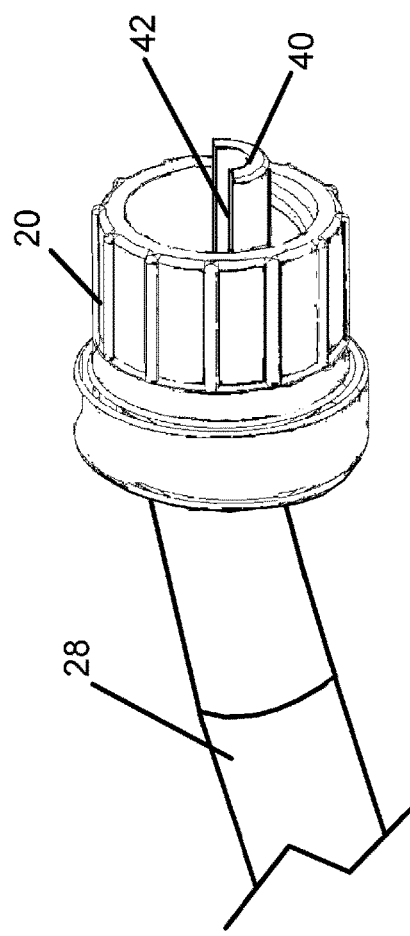
FIG. 3 depicts a perspective view of the sealing connector of FIG. 2, showing a threaded means for removable engagement and showing an alignment guide means in the form of a U-shaped alignment guide adapted for easy cleaning.

As shown, in FIGS. 1 and 1a, an interfacing docking component 22 may be placed in sealed engagement at a first end to a mating connector 25 which is in sealed engagement with the check valve 18 and has a passage therethrough communicating with the central conduit 19 at the first end of the check valve 18. On the opposite end of the docking component 22 from the connection to mating connector 25, the axial conduit 30 providing a pathway to communicate the negative pressure to the central conduit 19 is placed in a sealed engagement with the passage through the docking component 22 using means for sealed engagement thereto. This means for sealed engagement with the passage is currently provided by a seal which is formed by the threaded engagement and a resulting compression of an O-ring or pliable washer 32 or other sealing means to maintain the sealed communication of the vacuum in the axial conduit 30 with the central conduit 19 when the threaded luer lock 20 is engaged to operating threads on the docking component 22.

When the docking component 22 is employed, this sealed engagement of the axial conduit 30 through the passage 24 of the docking component 22 to the central conduit 19 at the second end of the check valve 18 thereby provides a continuous sealed passageway for fluid to exit the patient in a single direction, and to prevent any backflow into the lungs by the closure of the check valve 18 upon removal of the vacuum from the axial conduit 30 by a closure of the valve 36 between the vacuum source and the conduit 30 of the catheter 28. This valve 36 as noted provides a manual means to engage and disengage the negative pressure and control the fluid flow out of the patient as desired.

Particularly preferred in the device 10, the means for sealed connection such as the depicted luer lock 20, which engages with the docking component 22 or directly engages with the check valve 18 if properly configured employs a unique U-shaped guide 40, to align it with the passage 24 through the docking component 22 or with the conduit 19 of the check valve 18. The guide 40 provides both a means of alignment of the connectors such as the luer lock 20 and the passage 24 or the central conduit 19 by an insertion of the guide 40 into the passage 24 or central conduit 19 depending on the mode of connection. More importantly, and particularly preferred to prevent infection, the open U-shaped guide 40 also has an elongated opening 42 which provides a means for cleaning access to the inside surface of the U-shaped guide 40 which is most important in a hospital environment where germs abound and connections provide direct conduits into the body of patients from outside. Consequently, using any means for sealed engagement or connection, this guide 40 with an elongated opening 42 is preferred.

While all of the fundamental characteristics and features of the pleural effusion drainage device and method herein have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. An apparatus for treatment of a pleural effusion comprising:
a tube, said tube having a distal end adapted to communicate with fluid within a patient's body when placed in communication therewith in a mounted position;
said tube having a first end opposite said distal end;
an axial cavity communicating between said first end and said distal end of said tube;
a valve, said valve having a valve conduit running from a first end at said first end of said valve, to a second end of said valve conduit at said second end of said valve;
said first end of said valve conduit in a sealed engagement with said axial cavity at said first end of said tube;
said second end of said valve configured for a removable engagement with a connector on one end of a second tube, said removable engagement forming a sealed connection with an axial passage of said second tube;
said valve is configured to default to a closed position, thereby preventing communication through said valve conduit from said second end thereof to said axial cavity;
said valve is configured to be actuatable from said closed position to an open position by attaching said connector to said removable engagement of said second end of said valve, wherein communication of negative pressure in said axial passage of said second tube for a duration of said attachment of said connector to said removable engagement actuates said valve from said closed position to said open position;
said communication of negative pressure to said second end of said valve conduit is adapted to induce a flow of said fluid though said axial cavity of said tube in a first direction running only toward said first end of said tube;
said valve is configured to return to said closed position, thereby preventing said flow of said fluid from reversing from said first direction, upon disconnection of said removable engagement; and
said connector has an axial passage running substantially longitudinally through said connector and when viewed along said axial passage a guide member forms a U-shaped projection extending along said axial passage, said U-shaped projection terminating in a U-shaped distal surface substantially within a plane that is substantially perpendicular to the axial passage, said U-shaped projection and U-shaped distal surface of said guide member defining an elongated opening which provides for cleaning access to the inside surface of said guide member.

2. The apparatus for treatment of a pleural effusion of claim 1, additionally comprising: said guide member extending from said connector engaged with said second tube; and said guide member sized for sliding insertion into said second end of said valve conduit thereby defining a sliding guide for said connector to said removable engagement with said second end of said valve.

3. The apparatus for treatment of a pleural effusion of claim 2, additionally comprising: a second valve, said second valve having a passage therethrough communicating from a first end to a second end; said second end of said passage adapted for sealed communication with a source of said negative pressure; said first end of said axial passage of said second tube adapted for said sealed communication with said first end of said passage of said second valve; and said second valve configured for actuation between a closed position preventing communication of said negative pressure to said axial passage to an open position allowing communication of said negative pressure to said axial passage, whereby said negative pressure may be selectively communicated to said second end of said valve conduit.

4. The apparatus for treatment of a pleural effusion of claim 3, additionally comprising: said source of said negative pressure being a vacuum bottle.

5. The apparatus for treatment of a pleural effusion of claim 1, additionally comprising: a second valve, said second valve having a passage therethrough communicating from a first end to a second end; said second end of said passage adapted for sealed communication with a source of said negative pressure; said first end of said axial passage of said second tube adapted for said sealed communication with said first end of said passage of said second valve; and said second valve configured for actuation between a closed position preventing communication of said negative pressure to said axial passage to an open position allowing communication of said negative pressure to said axial passage, whereby said negative pressure may be selectively communicated to said second end of said valve conduit.

6. The apparatus for treatment of a pleural effusion of claim 5, additionally comprising: said source of said negative pressure being a vacuum bottle.

7. The apparatus for treatment of a pleural effusion of claim 1 wherein said second end of said valve is configured as a female luer connector and said connector on said second tube is a male luer connector.

* * * * *